United States Patent [19]

Dowling, Jr. et al.

[11] Patent Number: 4,932,776
[45] Date of Patent: Jun. 12, 1990

[54] FINGERPRINT ACQUISITION SYSTEM

[75] Inventors: Robert F. Dowling, Jr., Woodstock; Keith L. Knowlston, Brooklyn, both of Conn.

[73] Assignee: Fingerprint Technology, Inc., Pomfret, Conn.

[21] Appl. No.: 116,794

[22] Filed: Nov. 5, 1987

[51] Int. Cl.⁵ .............................................. G06K 9/00
[52] U.S. Cl. ............................................................ 356/71
[58] Field of Search ............ 356/71; 350/96.25, 96.26, 350/96.27; 382/4, 5; 364/62

[56] References Cited

U.S. PATENT DOCUMENTS

| | | | |
|---|---|---|---|
| 3,174,414 | 3/1965 | Myer | 356/71 |
| 3,247,756 | 4/1966 | Siegmund . | |
| 3,323,407 | 6/1967 | Gamba . | |
| 3,435,244 | 3/1969 | Burckhardt et al. . | |
| 3,449,036 | 6/1969 | Jacobsen | 390/96.25 |
| 3,453,596 | 7/1969 | Hawkins . | |
| 3,630,612 | 12/1971 | Lehovec . | |
| 3,648,240 | 5/1972 | Jacoby et al. . | |
| 3,668,633 | 6/1972 | Sadowsky . | |
| 3,906,520 | 9/1975 | Phillips | 354/62 |
| 3,982,836 | 9/1976 | Green et al. | 356/71 |
| 4,032,889 | 6/1977 | Nassimbene . | |
| 4,120,585 | 10/1978 | DePalma et al. . | |
| 4,206,441 | 6/1980 | Kondo | 356/71 |
| 4,210,899 | 7/1980 | Swonger et al. . | |
| 4,322,163 | 3/1982 | Schiller . | |
| 4,340,330 | 7/1982 | Ruell | 356/71 |
| 4,537,484 | 8/1985 | Fowler et al. . | |
| 4,544,267 | 10/1985 | Schiller . | |
| 4,544,842 | 10/1985 | Engemann et al. . | |
| 4,547,668 | 10/1985 | Tsikos . | |
| 4,553,837 | 11/1985 | Marcus . | |
| 4,569,080 | 2/1986 | Schiller . | |
| 4,570,063 | 2/1986 | De Bie et al. | 350/96.25 |
| 4,582,985 | 4/1986 | Lofberg . | |
| 4,601,537 | 7/1986 | Saccocio | 350/96.27 |
| 4,671,612 | 7/1987 | Sakurai et al. . | |
| 4,785,171 | 11/1988 | Dowling et al. | 356/71 |

OTHER PUBLICATIONS

West et al "Fingerprint-based Person Verification System" *IBM Technical Disclosure Bulletin,* vol. 17, No. 12 (May 1975) pp. 3741-3743.

*Primary Examiner*—Richard A. Rosenberger
*Attorney, Agent, or Firm*—Hayes & Reinsmith

[57] ABSTRACT

A characteristic pattern acquisition system featuring a block formed of a bundle of optical fibers and having one end face for projecting an image of a characteristic pattern placed on an opposite detecting end face of the block and a light source for projecting light onto the detecting end face to illuminate the characteristic pattern.

10 Claims, 5 Drawing Sheets

FINGERPRINT ACQUISITION SYSTEM

BACKGROUND OF THE INVENTION

This invention relates to a system for acquiring fingerprints and other characteristic patterns and, more specifically, a system utilizing a fiberoptic block to detect and transmit a characteristic pattern for electronic analysis.

Several fingerprint acquisition systems have been reported in the art.

U.S. Pat. No. 3,668,633 to Sadowsky discloses the use of separate arrays of optical fibers for transmitting light to a finger and for receiving a fingerprint reflection.

U.S. Pat. No. 4,582,985 to Lofberg discloses the use of an array of sensing elements to detect a fingerprint. Each sensing element is attached to a single optical fiber which carries light from a LED to a finger and which also carries light reflected from the fingerprint back to a photo transistor which then processes the fingerprint image electronically. The finger is disclosed as being spaced from the fiber end which is shown as having an end face slightly curved but generally perpendicular to its axis.

A number of other patents disclose the use of transparent blocks upon which a finger is placed and through which a detecting light signal is internally reflected at less than the critical angle with respect to the block surface. The internally reflected light signals carry the image of the fingerprint as a result of selected light absorption at the fingerprint ridges. These patents are U.S. Pat. Nos. 4,120,585 to De Palma et al; 4,553,837 to Marcus; 4,210,899 to Swonger et al; 4,537,484 to Fowler et al; 4,032,889 to Nassimbene; and 4,544,267 and 4,322,163, both to Schiller.

These prior art fingerprint acquisition systems in general utilize relatively large, complex, costly and fragile components, especially those adapted for detecting the fingerprint itself. In addition, these systems do not always offer the high resolution and detail required for high accuracy fingerprint definition. Because of such problems these conventional systems are typically not suited for widespread use and are generally confined to a narrow range of applications which justify complexity and expense.

In U.S. Pat. No. 4,785,171 entitled Fingerprint Acquisition System, assigned to the assignee of this invention, there is disclosed a characteristic pattern acquisition system especially adapted for fingerprints which utilizes a fiberoptic block having an angled detecting end face and an imaging end face opposite the detecting end face. The fiberoptic block is made up of a bundle of optical fibers the opposite ends of which terminate in and form the detecting and imaging end faces. The individual fiber detecting end faces are angled such that parallel light rays traveling from the imaging end to the detecting end are internally reflected so that they exit through the side of the detecting end, while at least a portion of non-parallel light rays are permitted to internally reflect at the fiber detecting end face and reverse direction in the fiber. This system utilizes a light source which directs light rays in through the imaging end to be selectively absorbed by a fingerprint or other characteristic pattern at the detecting end face. The non-absorbed non-parallel light rays return to the imaging end and form the image of the characteristic pattern thereon. A video camera records the image for further electronic processing. While this characteristic pattern acquisition system works well, the injection of light through the imaging end poses the possibility of specular reflection of the light source off the optical surface formed by the polished imaging end face and into the video camera, and it will be understood that any camera and lens system inherently require accommodation for the size and fragility of the components. In addition, the mere presence of separate optical surfaces for the fiberoptic block imaging end face and for the video camera lens introduce potential for disruption of the image acquisition, for example, were the optical surfaces to become dirty or fogged.

OBJECTS OF THE INVENTION

With such problems in mind, it is therefore an object of this invention to provide a system means for acquiring fingerprints and other characteristic patterns which offers considerable simplicity in design and construction.

It is another object of this invention to provide a characteristic pattern acquisition system which eliminates the problem of light source reflection off an optical surface.

It is a further object of this invention to provide a characteristic pattern acquisition system which utilizes a minimum of separate optical surfaces.

It is yet another object of this invention to provide a characteristic pattern acquisition system which is of particularly rigid construction for high durability in repeated use.

It is a further object of this invention to provide a means for acquiring fingerprints and other characteristic patterns which is relatively immune to adverse environmental effects.

It is another object of this invention to provide an improved fingerprint acquisition system which is of compact size.

Other objects will be in part obvious and in part pointed out in more detail hereinafter.

A better understanding of the objects, advantages, features, properties and relations of the invention will be obtained from the following detailed description and accompanying drawings which set forth certain illustrative embodiments and are indicative of various ways in which the principles of the invention are employed.

SUMMARY OF THE INVENTION

The present invention provides a characteristic pattern acquisition system comprising a fiberoptic block having a first end face for detecting a characteristic pattern placed thereon and a second imaging end face, opposite the first detecting end face, for projecting an image of a characteristic pattern placed upon the detecting end face, the fiberoptic block comprising a bundle of optical fibers having light ray-guiding cores, the optical fibers having opposite end faces terminating in and forming the detecting and imaging end faces, respectively; a light source for projecting light and illuminating a characteristic pattern placed on the fiberoptic block detecting end face; and means for electronically transmitting the image, from the fiberoptic block imaging end face, of a characteristic pattern placed upon the fiberoptic block detecting end face. In the preferred embodiment, the electronic image transmitting means comprises a solid state image sensor immediately adjacent and bonded to the fiberoptic block imaging end face.

DETAILED DESCRIPTION OF A PREFERRED EMBODIMENT OF THE INVENTION

The present invention relates to a system which is adapted to electronically acquire various characteristic patterns using fiberoptic and electronic components. The image data from the characteristic patterns which are acquired with the aid of this invention may be electronically transmitted to a computer memory or other electronic device using known pattern recognition technology. The stored characteristic pattern may be then recalled at any time and electronically compared to another characteristic pattern to determine a match therebetween.

While the present invention is preferably adapted for a fingerprint or other skin print, the term "characteristic pattern" is not to be so limited since the present invention is useful with various other types of characteristic patterns, as will be hereinafter seen. This invention is contemplated to be particularly useful for security purposes by controlling access to certain areas or equipment. Other applications will become obvious as the reader gains understanding in the way in which the system functions.

Figure 1:
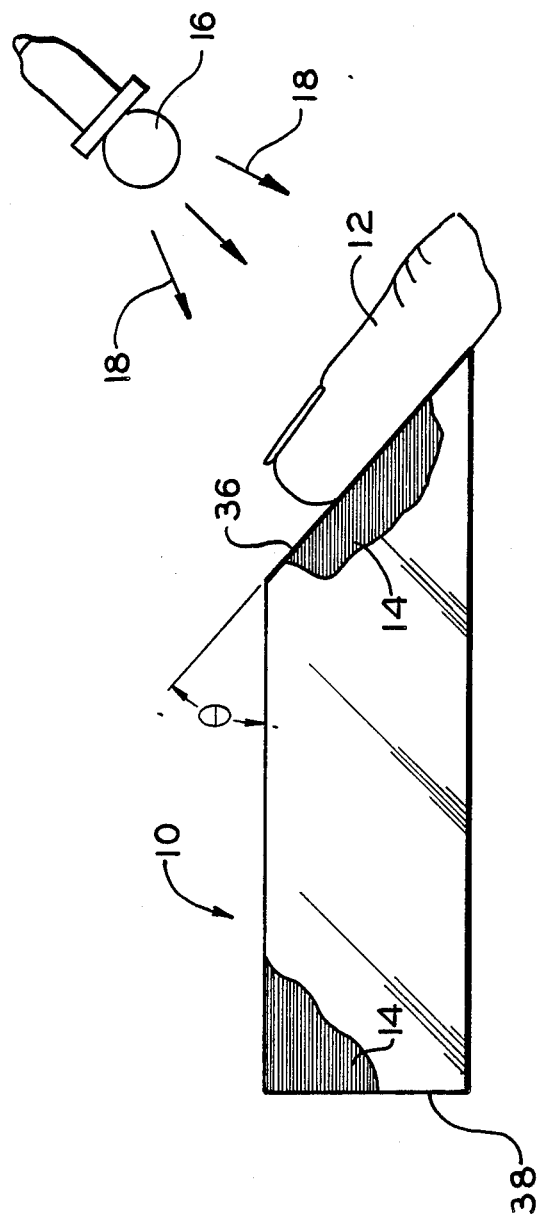
FIG. 1 is a side view, partly in section and partly broken away, of a fiberoptic block of this invention in relation to a light source for transilluminating a print of a finger placed on a detecting end face of the block.
Figure 2:
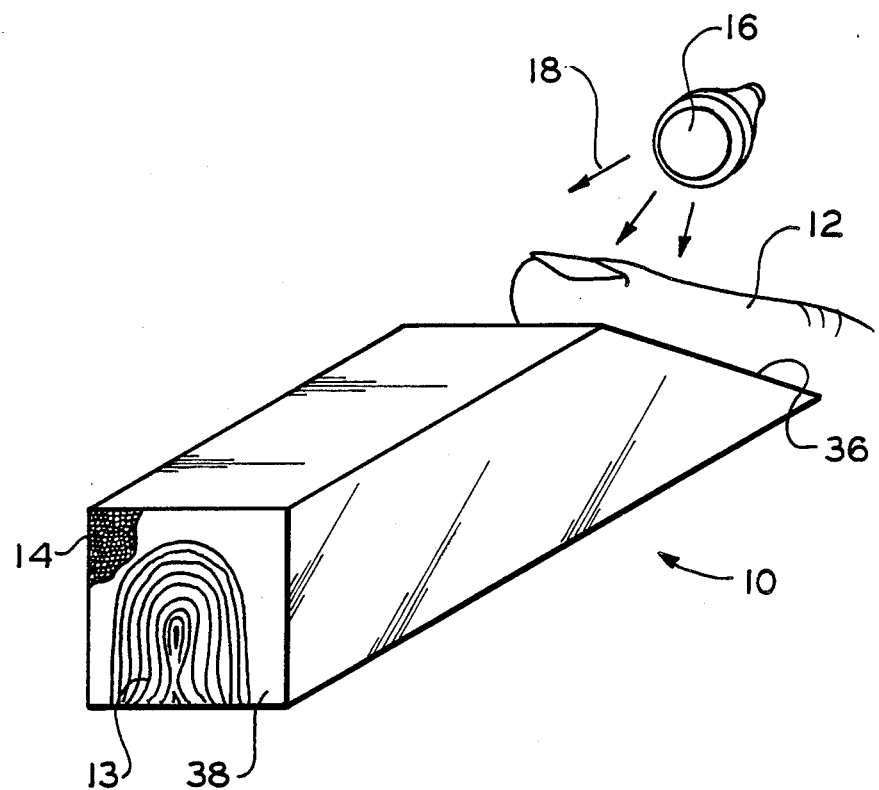
FIG. 2 is a perspective view, partly in section and partly broken away, of the embodiment of FIG. 1 showing the image of a fingerprint at an imaging end face of the fiberoptic block.

In FIGS. 1 and 2 there are shown, respectively, side and perspective views of a fiberoptic block and light source of the present invention as they are used in acquiring a print from a finger of an individual. Fiberoptic block 10 comprises a plurality of individual optical fibers 14 which are arrayed in a bundle to make up block 10. Each optical fiber 14 is of conventional structure and includes a light-guiding core for transmitting light rays from one end of each fiber to its opposite end. Clad optical fibers are preferred in this invention, with the cladding material having an index of refraction lower than that of the light-guiding core, thereby enabling non-parallel light rays within the core to be reflected at the core/cladding interface and propagated through the length of the core. Any known type of optical fiber may be utilized in the fiberoptic block, for example, optical fibers having cores of glass, fused silica or a polymer such as an acrylate or methacrylate. Any of the conventional glass or polymer cladding materials may be utilized as well. Preferably, the optical fiber core and cladding are composed of a Schott type F2 flint glass, and Schott type 8250 borosilicate, respectively, with indicies of refraction of 1.62 and 1.48, respectively. These types of glass are available from Schott Optical Company, Duryea, PA.

The individual optical fibers 14 are in essentially parallel relationship and maybe secured in the block arrangement by any conventional technique, such as fusion, adhesive or confinement by mechanical means. The fusion technique is preferable, for example, as taught in U.S. Pat. No. 3,247,756 to Siegmund.

A first detecting end 36 of fiberoptic block 10 comprises the polished core exposed end faces of the individual optical fibers 14 which are at an acute angle "theta" with respect to the longitudinal axis of the individual fibers and of the block. A finger 12 is shown placed upon the detecting end surface 36, and a light source 16 emitting light rays 18 is shown transilluminating finger 12 on detecting end face 36. As will be explained hereinafter, the image of a fingerprint 13 of finger 12 is displayed on the imaging end face 38 of fiberoptic block 10 (FIG. 2). Imaging end face 38 is opposite detecting end 36 and comprises the polished core-exposed end faces of the individual optical fibers 14. These fiber end faces are essentially perpendicular to the longitudinal axis of the individual fibers 14 and of the fiberoptic block 10.

In accordance with this invention, the characteristic pattern illumination technique used in the disclosed preferred embodiment is transillumination. For this technique to be useful, the body or structure to which the characteristic pattern is attached must be sufficiently translucent so that light rays from a light source 16 may pass through that body or object. Where it is desired to obtain a characteristic pattern for fingerprints as shown in FIGS. 1 and 2, the light source may be simply a high intensity incandescent light bulb.

Detecting end face 36 should be of sufficient size and area to receive the characteristic pattern to be acquired. Thus, in the example shown, the width and height of the fiberoptic block 10 need only be of comparable or slightly larger area than the end of a finger. Where larger characteristic patterns are desired to be acquired, for example, palm prints, footprints or other patterns, the size of the fiberoptic block 10 and of the detecting end face 36 is adjusted accordingly.

Figure 3:
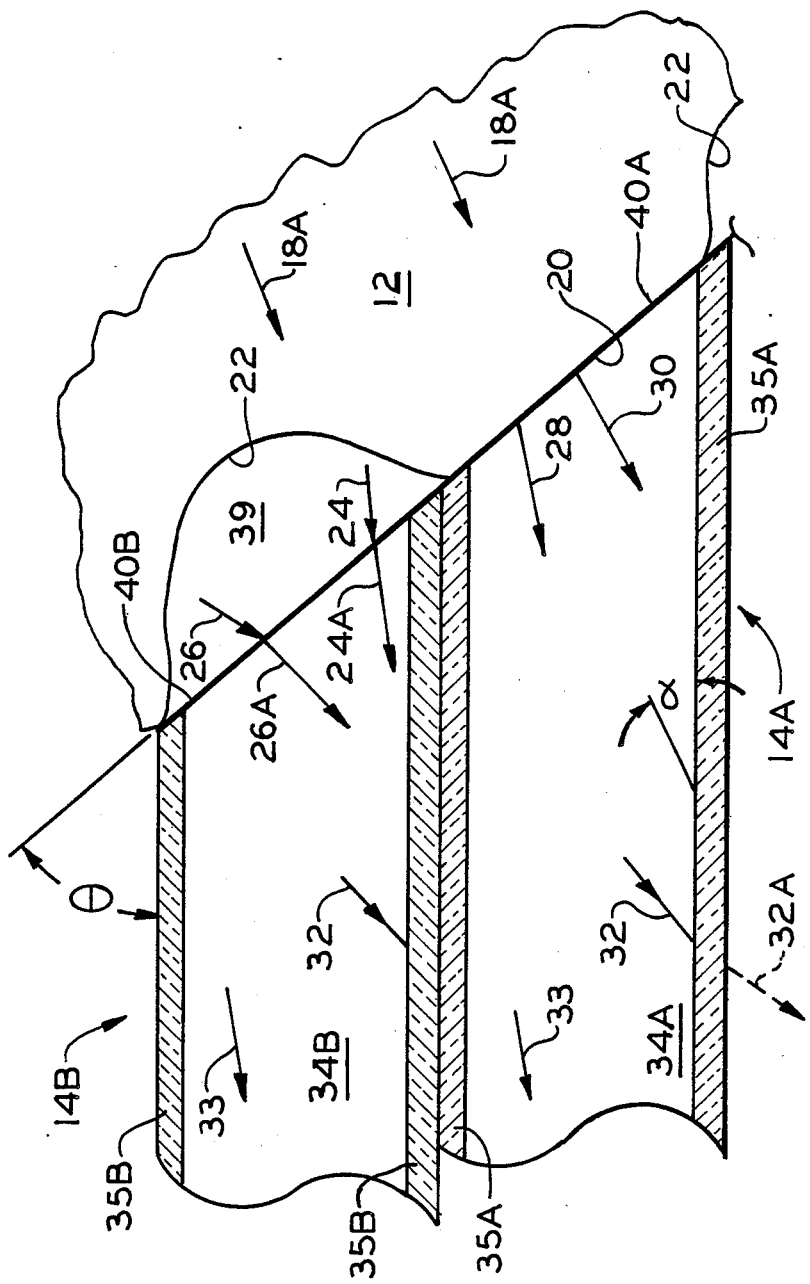
FIG. 3 is an enlarged longitudinal cross-sectional view, partly broken away, of the angled detecting end of individual optical fibers of the fiberoptic block of FIG. 1.

The transmission of light rays 18 through finger 12 and into the individual optical fibers 14 is shown in detail in FIG. 3. Individual optical fibers 14a and 14b each have a light transmitting core 34a, 34b surrounded by a lower refractive index cladding layer 35a, 35b. Angled end face 40a, 40b of fibers 14a and 14b exposes the core 34a, 34b and is angled at acute angle "theta" with respect to the fiber longitudinal axis. The preferable diameter of optical fibers 14a and 14b is from about 3 to about 50 microns.

As a finger is placed on the fiberoptic block detecting end face, individual fingerprint ridges come in contact with the individual core exposing fiber end faces. Fingerprint valleys are between the fingerprint ridges and are separated from the individual optical fiber end faces by a gap. For purposes of illustration only, FIG. 3 shows a fingerprint ridge 20 in direct contact with end face 40a of fiber 14a, while adjacent fingerprint valley 22 is shown separated by air gap 39 from end face 40b of fiber 14b. Although the fingerprint ridge and valley shown in FIG. 3 are of similar size to fibers 14a and 14b, in the preferred embodiment of this invention, it is to be understood that the diameter of fibers 14 will be significantly smaller than the width of a fingerprint ridge or valley. Light rays 18a from a light source are shown passing through finger 12 to transilluminate the fingerprint pattern.

As light rays 18a pass through an individual fingerprint ridge 20, they cause the fingerprint ridge to glow and transmit light rays 28 and 30 through the interface between the ridge 20 and the optical fiber 14a end face 40a and into the interior of the fiber core 34a. These light rays 28 and 30 pass through essentially without any appreciable gap between the finger ridge 20 and fiber end face 40a, whereupon the light rays propagate into the fiber core 34 at different angles as shown. Only those light rays 33 within fiber core 34 which have an angle no greater than angle "alpha" (FIG. 3) with respect to the fiber longitudinal axis will be totally reflected so as to be propagated down the full length of the fiber. Those rays 32 which have an angle greater than angle "alpha", the critical angle, will be partially refracted into the cladding 35a and out of the fiber 14a as shown by light ray 32a. Angle "alpha" is determined by Snell's Law and is dependent on the refractive indices of the fiber core and cladding. Because of the direct coupling of finger ridge 20 to optical fiber surface 40a, a relatively large number of light rays will be propagated at less than the critical angle "alpha" down the length of optical fiber 14a.

Those light rays such as 24, 26 which are emitted from the valleys 22 of finger 12 pass through air space 39 and are shown as rays 24a and 26a, respectively, entering fiber core 34b through end face 40b. Because of the passage of these light rays through the air gap and an additional interface, they are of less intensity than those emitted from the directly coupled fingerprint ridges 20. Although the effect is not fully understood, it is believed that because of the acute angle "theta" of fiber end face 40, a significant number of these light rays 24a and 26a will be propagated into fiber core 34b at an angle greater than the critical angle "alpha" and refracted out through fiber cladding 35b. Consequently, fewer of these fingerprint valley emitted light rays will be transmitted down the full length of optical fiber 14b. It has been found that the described effect with the fiber detecting end faces contained in a common plane at angle "theta" improves the resolution of the image projected onto the opposite fiber ends which make up the fiberoptic block imaging end face 38. A preferred range of angles "theta" for the optical fibers 14 is from about 30° to about 60°, with about a 45° angle being preferred.

As a result of the transillumination lighting system, the portions of the fingerprint image 13 (FIG. 2) which depict fingerprint ridges will be shown as illuminated areas while those portions which depict fingerprint valleys will be shown as darkened areas.

It should also be noted that characteristic patterns which do not have alternating regions of contact and gaps with the fiber detecting end faces can also be acquired by the present invention if they comprise regions having different degrees of transparency to light.

Figure 4:
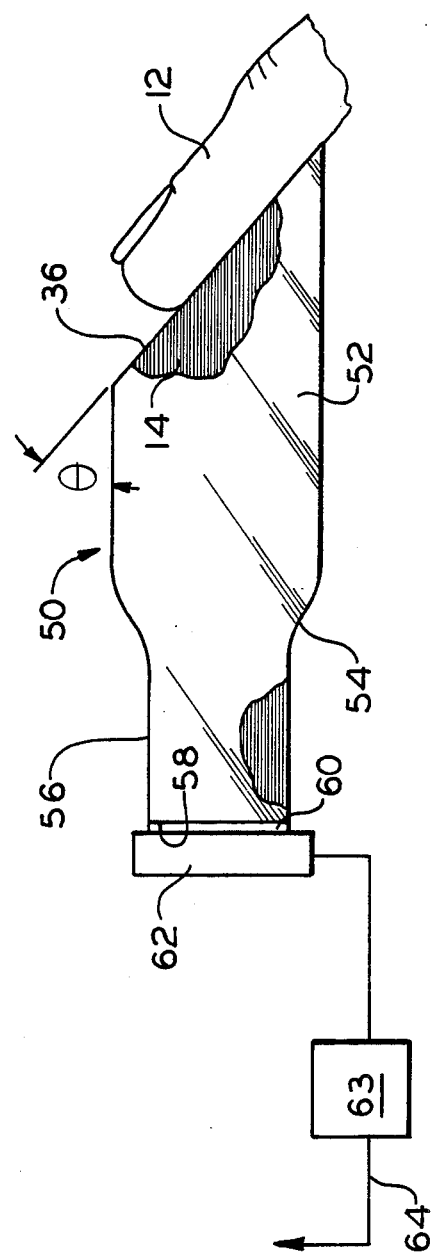
FIG. 4 is a longitudinal side view, partly in section and partly broken away, of the fiberoptic block of this invention and a preferred embodiment of an electronic image transmitting device.

To electronically transmit the fingerprint image 13 from imaging end face 38 in accordance with this invention, there is shown in FIG. 4 a preferred embodiment where a solid state image sensor 62 is used to detect and transmit an image. Solid state image sensor 62, which is preferably a charged coupled device (CCD), is secured immediately adjacent to the fiberoptic block imaging end face. A layer 60 of optically transparent adhesive, for example, epoxy, is shown bonding the sensing face of the solid state image sensor 62 directly to the imaging end face 58 of fiberoptic block 50. Because detector 62 is bonded and coupled directly to imaging end face 58 of fiberoptic block 50, there is no separate optical surface therebetween such as the lens of a camera. By virtue of such construction, the absence of any such additional optical surface eliminates any problem of contamination of that surface which might otherwise reduce the quality of the characteristic pattern image detected by sensor 62 and transmitted to computer 63. In addition, potential problems inherently caused by the size and fragility of a camera and lens system are obviated. Furthermore, where the finger 12 placed on detecting end face 36 is transilluminated, there is no need for the injection of light through the imaging end face 58 which additionally eliminates potential light reflection problems between end face 58 and image sensor 62.

While the transillumination system is preferred with the embodiment shown in FIG. 4, it is to be understood that the present invention is not limited to this type of illumination since LED or other relatively small light sources might be implanted in the face of image sensor 62 to transmit light through the imaging end face and acquire the characteristic pattern image in the manner disclosed in the above referenced U.S. Pat. No. 4,785,171. The light source may even be infrared if a silicon based sensor is used.

If desired, computer 63 may include means to match the characteristic pattern image with another characteristic pattern image to activate or control an access security device, e.g., by signal 64.

Because the sensing surface of CCD type image sensor 62 is typically smaller than the axial cross-sectional size of a fiberoptic block used to acquire a fingerprint, the imaging end portion 56 of fiberoptic block 50 may be tapered down in size to correspond with the area of image sensor 62 as shown in FIG. 4.

Where the individual optical fibers 14 of a fiberoptic block are fused together, the imaging end portion 56 of the fiberoptic block may be heated and drawn to reduce the size of the imaging end face 58 and correspondingly reduce the diameter of each of the optical fibers 14 which make up the imaging end of fiberoptic block 50. The degree of angle of taper between the detecting end 52 and the imaging end 56 should be such that there is no significant or material light loss in the optical fibers 14 as they travel between the detecting and imaging end faces. The proper parameters for tapering the imaging end 56 may be determined by simple experimentation.

A reduction in the diameter of the fibers would increase the resolution of the image and thus create the capacity for greater detail. However, this increased number of fibers also increases the cost of the block. The optimum number and size of the fibers 14 can be determined by simple experimentation for each application. For acquiring individual fingerprints, the size of the fiberoptic block at the detecting end face would typically be approximately 1.25 inches square.

Because the actual characteristic pattern is placed on the fiberoptic block angled detecting end face 36 and the fingerprint image is projected onto the opposite fiberoptic block imaging end face 58, the fingerprint image length is reduced by the ratio of the corresponding lengths of the two fiberoptic block ends. The width of the characteristic pattern image remains unchanged. This length reduction would be of minimal concern in the system where all of the characteristic pattern images stored for comparison were acquired from fiberoptic blocks having the same angle detecting end face. However, if this system were to be used to compare a shortened image with an image from a block or other device which has not been so shortened, means should then be provided to restore the shortened image to actual size so that the correct comparisons may be made. This may be done by programming a conventional digital computer 63 with well known programs in the industry, one such program being sold under the name "Image Pro" developed and marketed by Media Cybernetics Company, Silver Springs, MD.

Figure 5:
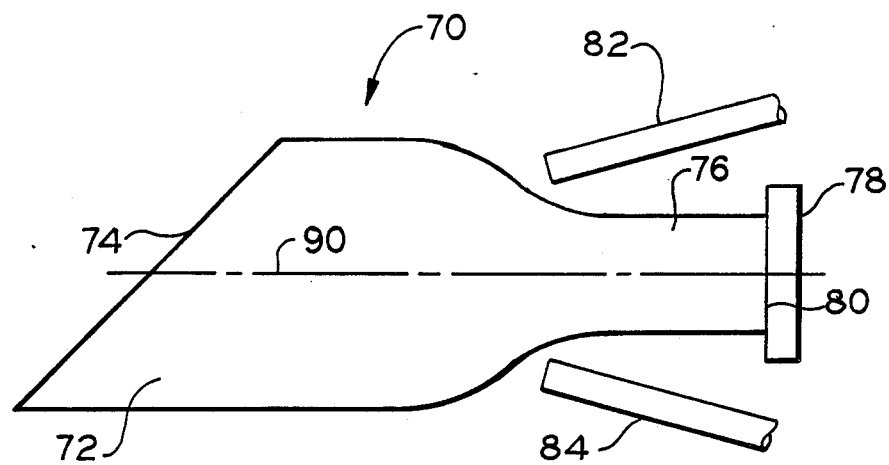
FIG. 5 is a longitudinal side view, partly broken away, of another embodiment of this invention.
Figure 6:
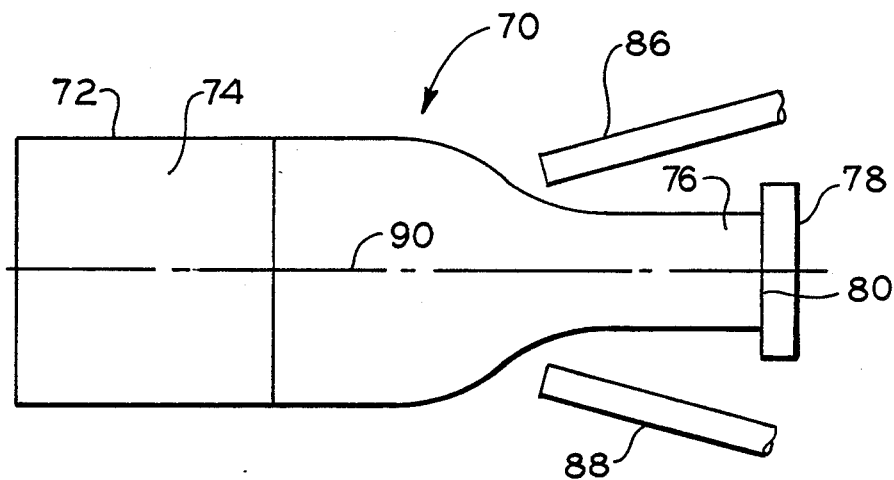
FIG. 6 is plan view, partly broken away, of the embodiment of FIG. 5.

Referring now to that embodiment illustrated in FIGS. 5 and 6, side illumination of a fiberoptic block 70 of this invention is disclosed wherein light is injected into sides of block 70 at an angle. That light is directed toward angled detecting end face 74 of the block 70, upon which a finger, for example, may be placed. Thus, light is directed in a direction opposite an imaging end 76 of block 70 with its image sensor 78 secured to face 80. As in the previously described embodiment, block 70 is formed of a multiplicity of parallel fibers bundled together and fixed in the form of a block which is cut at one end at an angle of about 45° to longitudinal axes of the fibers and at an angle of about 90° at the opposite end of the block. To maximize light transmission, both ends 72 and 76 of block 70 are polished. The described side illumination may be accomplished with conventional incandescent lamps and lenses, or both, or with fiber optic bundles such as shown at 82 and 84 shown on upper and lower sides of block 70 in FIG. 5. Bundles 86 and 88 are shown in FIG. 6 located on opposite lateral sides of block 70. Each bundle 82, 84, 86, 88 is shown pointing toward angled detecting end 72 of block 70, preferably at an angle of about 30° to 45° relative to its major longitudinal axis 90.

To produce a more uniform image, it has been found that better results may be obtained when four separate bundles, as described above, of fiber optics are used, with one bundle being mounted in any suitable manner on each side of a four sided block of generally square cross-section. Each bundle is suitably mounted at a predetermined angular orientation as described above relative to the longitudinal axis 90 of block 70 and is generally directed toward the detecting end face 74 of block 70. In this manner, the bundles such as at 82, 84, 86, 88 collectively form a generally square light source which injects substantially equal amounts of light into each discrete side of block 70 and thus produces the more uniform image of a fingerprint or other characteristic pattern at tapered imaging end 76 where the CCD array is secured by an optically clear epoxy. By virtue of this described side illumination technique, light actually passes through block 70; light in block 70 may be absorbed by a finger, not shown, which produces an illuminated image at the detecting end face 74 with darkened or black areas which depict fingerprint ridges on a white or illuminated background depicting fingerprint valleys.

Other than this described side illumination technique, the characteristic pattern acquisition system of this embodiment of FIGS. 5 and 6 functions the same as the previously described imaging end transillumination system of the embodiment. As in the previously described embodiment, the invention shown in FIGS. 5 and 6 is particularly rugged and is of significantly reduced size while having only one optical surface, the angled face 74 which can be readily cleaned.

In addition, each of the described constructions of this invention serve to minimize any distortion by eliminating any lens associated with a camera as is more commonly required. Elimination of such a camera lens not only removes any distortion that a camera lens would normally introduce into the system, but further eliminates optical lens surfaces which may reflect light and undesirability reduce contrast and also "fog" over upon being subjected to rapid temperature change.

Thus, as described above, the present invention provides a means for acquiring characteristic patterns which is simple in design and construction while being rugged and durable for repeated use. The high resolution available with the disclosed fiberoptic block makes this invention highly useful for widespread security applications where fingerprints or other characteristic patterns are used for identification. The electronic output of the desired characteristic pattern image may be transmitted by wire, radio or other transmission means to conventional computer systems for comparison and matching with other stored patterns.

As will be apparent to persons skilled in the art, various modifications, adaptations and variations of the foregoing specific disclosure can be made without departing from the spirit and scope of this invention.

We claim:

1. A fingerprint acquisition system comprising a fiberoptic block having a first end face for detecting a fingerprint pattern of a finger placed thereon and a second imaging end face, the second imaging end face being opposite the first detecting end face for projecting an image of a fingerprint pattern of said finger placed upon said detecting end face, said fiberoptic block comprising a bundle of optical fibers having light ray-guided cores, the optical fibers having opposite end faces terminating in and respectively forming said detecting and imaging end faces, a solid state image sensor for electronically transmitting the image, from said fiberoptic block imaging end face, of a fingerprint pattern of a finger placed upon said fiberoptic block detecting end face, said solid state image sensor being bonded to said fiberoptic block imaging end face, means for comparing the electronically transmitted fingerprint pattern image with another image and determining a match therebetween, and a light source for projecting light onto said fiberoptic block detecting end face to transilluminate the fingerprint pattern of a finger placed thereon.

2. The system of claim 1 wherein each of the individual optical fiber detecting end faces are at an acute angle with respect to the optical fiber longitudinal axis, and wherein said detecting end faces of the individual optical fibers are contained in a common plane.

3. The system of claim 2 wherein said fiberoptic block detecting end face and said individual optical fiber angled end faces have an angle from about 30° to about 60°, relative to the axis of said optical fibers at said detecting end.

4. The system of claim 1 wherein the ends of the optical fibers at the first detecting end of said fiberoptic block are in an adjacent, essentially parallel relationship, and wherein the ends of the optical fibers at the second imaging end are in an adjacent, essentially parallel relationship.

5. The system of claim 1 wherein said fiberoptic block imaging end face is smaller than said fiberoptic block detecting end face, and wherein the diameter of each of the individual fibers at the fiber imaging end faces is smaller than the diameter at the fiber detecting end faces.

6. The system of claim 5 wherein said fiberoptic block tapers down in cross-sectional area from said detecting end to said imaging end.

7. The system of claim 1 wherein said optical fibers in said fiberoptic block have a diameter of from about 3 to about 50 microns.

8. The system of claim 1 wherein said image comparing means comprises a digital computer for storing, retrieving and comparing fingerprint patterns.

9. The system of claim 1 further including means for activating an access device operable by said comparing and match determining means.

10. The system of claim 1 including electronic means to correct shortening of a characteristic pattern detected by said fiberoptic block.

* * * * *